(12) United States Patent
Ginot et al.

(10) Patent No.: US 7,553,621 B2
(45) Date of Patent: Jun. 30, 2009

(54) READING, DETECTION OR QUANTIFICATION METHOD, HYBRIDS OR COMPLEXES USED IN SAID METHOD AND THE BIOCHIP USING SAME

(75) Inventors: Frederic Ginot, Voreppe (FR); Dominique Masse, Coublevie (FR); Arnelle Novelli-Rousseau, Seyssins (FR); Severine Moutin, Varces Allieres & Risset (FR)

(73) Assignees: BioMerieux, Marcy l'Etoile (FR); Commissariat A l'Energie Atomique, Paris (FR)

( * ) Notice: Subject to any disclaimer, the term of this patent is extended or adjusted under 35 U.S.C. 154(b) by 529 days.

(21) Appl. No.: 10/488,587

(22) PCT Filed: Sep. 9, 2002

(86) PCT No.: PCT/FR02/03052

§ 371 (c)(1),
(2), (4) Date: Apr. 1, 2004

(87) PCT Pub. No.: WO03/023061

PCT Pub. Date: Mar. 20, 2003

(65) Prior Publication Data

US 2005/0142549 A1 Jun. 30, 2005

(30) Foreign Application Priority Data

Sep. 7, 2001 (FR) .................................. 01 11630

(51) Int. Cl.
*C12Q 1/68* (2006.01)
*G01N 33/53* (2006.01)
*C12M 1/34* (2006.01)
*C12M 3/00* (2006.01)

(52) U.S. Cl. ..................... 435/6; 435/7.1; 435/288.7

(58) Field of Classification Search ................ 435/6, 435/7.1, 288.6
See application file for complete search history.

(56) References Cited

U.S. PATENT DOCUMENTS 4,299,494 A 11/1981 Badoz et al.

(Continued)

FOREIGN PATENT DOCUMENTS

FR 2 813 207 3/2002

(Continued)

OTHER PUBLICATIONS

Hu et al., 1998, The FASEB J., 12: 1135-1142.*

(Continued)

*Primary Examiner*—Ram R. Shukla
*Assistant Examiner*—Robert T. Crow
(74) *Attorney, Agent, or Firm*—Oliff & Berridge, Plc.

(57) ABSTRACT

The invention relates to a method of reading, detecting or quantifying at least one biological reaction, on a support, between either a recognition molecule and a labeled target molecule or between a target molecule and a labeled detection molecule. The inventive method comprises treating the support under physicochemical conditions that allow the following: either the separation of the recognition molecule and the labeled target molecule or the separation of the target molecule and the labeled detection molecule. The inventive method further comprises producing images before and after the physicochemical treatment that can be used to determine the specific and non-specific bindings between the different molecules. The invention also relates to hybrids and complexes used in the inventive method and to a biochip containing the same which is used to carry out the inventive method. The invention is particularly suitable for use in the field of diagnosis.

46 Claims, 2 Drawing Sheets

U.S. PATENT DOCUMENTS

| | | | |
|---|---|---|---|
| 5,599,668 | A | 2/1997 | Stimpson et al. |
| 5,660,990 | A * | 8/1997 | Rao et al. ............... 435/6 |
| 5,753,444 | A | 5/1998 | Wu et al. |
| 5,756,011 | A * | 5/1998 | Woodhead et al. ......... 252/700 |
| 6,093,370 | A | 7/2000 | Yasuda et al. |
| 6,161,031 | A * | 12/2000 | Hochman et al. ......... 600/407 |
| 2001/0014449 | A1 | 8/2001 | Nerenberg et al. |

FOREIGN PATENT DOCUMENTS

| | | |
|---|---|---|
| WO | WO 91/19812 | 12/1991 |
| WO | WO 95/08000 | 3/1995 |
| WO | WO 97/27328 | 7/1997 |
| WO | WO 97/34909 | 9/1997 |
| WO | WO 97/45202 | 12/1997 |
| WO | WO 98/04740 | 2/1998 |
| WO | WO 98/47000 | 10/1998 |
| WO | WO 99/35500 | 7/1999 |
| WO | WO 99/65926 | 12/1999 |
| WO | WO 00/07982 | 2/2000 |
| WO | WO 00/71750 A1 | 11/2000 |
| WO | WO 00/78452 A1 | 12/2000 |
| WO | WO 01/23867 A1 | 4/2001 |
| WO | WO 01/40778 A1 | 6/2001 |
| WO | WO 01/45843 * | 6/2001 |
| WO | WO 02/40711 A1 | 5/2002 |

OTHER PUBLICATIONS

Strother et al., 2000, NAR 28: 3535-3541.*
GRB2, Santa Cruz Biotetech, data sheet, 1 page.*
Taton et al, Science, vol. 289, pp. 1757-1760 (Sep. 8, 2000).*

T. A. Taton et al., "Scanometric DNA Array Detection With Nanoparticle Probes," *Science* 289 (5485):1757-60, Sep. 8, 2000.
L. He et al., "Colloidal Au-Enhanced Surface Plasmon Resonance for Ultrasensitive Detection of DNA Hybridization," *J. Am. Chem. Soc.* 122:9071-77, 2000.
M. Chee et al.; "Accessing Genetic Information With High-Density DNA Arrays" *Science* 274(5287):610-14, Oct. 25, 1996.
A. Caviani Pease et al., "Light-generated Oligonucleotide Arrays for Rapid DNA Sequence Analysis," *Proc. Natl. Acad. Sci. USA* 91:5022-26, May 1994.
J. Chevalier et al., "Biotin and Digoxigenin as Labels for Light and Electron Microscopy in Situ Hybridization Probes: Where Do We Stand?" *J. Histochem. Cytochem.* 45(4):481-491, 1997.
J. H. W. Leuvering et al., "Sol Particle Immunoassay (SPIA)," *Journal of Immunoassay* 1(1):77-91, 1980.
A. Perrin et al., "Thyroid Stimulating Hormone Assays Based on the Detection of Gold Conjugates by Scanning Force Microscopy," *Analytical Biochemistry* 256:200-06, 1998.
A. Perrin et al., "Immunomagnetic Concentration of Antigens and Detection Based on a Scanning Force Microscopic Immunoassay," *Journal of Imunological Methods* 224:77-87, 1999.
K. Okano et al., "Using Microparticle Labeling and Counting for Attomole-Level Detection in Heterogeneous Immunoassay," *Anal. Biochem.* 202:120-25, 1992.
S. Kubitschko et al., "Sensitivity Enhancement of Optical Immunosensors with Nanoparticles," *Anal. Biochem.* 253(1):112-22, 1997.
G. Dreyer et al., "Sequence-Specific Cleavage of Single-Stranded DNA: Oligodeoxynucleotide-EDTA fe(II)," *Proc. Natl. Acad. Sci. USA* 82:968-72, Feb. 1985.

* cited by examiner

READING, DETECTION OR QUANTIFICATION METHOD, HYBRIDS OR COMPLEXES USED IN SAID METHOD AND THE BIOCHIP USING SAME

The present invention relates to a method of reading, a method of detecting and a method of quantifying chemical or biological reactions performed on a support, which support may consist of a Petri dish, a microtiter plate, a biochip and the like. The present invention also relates to a support comprising a plurality of, that is to say at least two, zones of molecular recognition, each recognition zone containing at least one recognition molecule. While there are at least two recognition molecules per recognition zone, all the recognition molecules are structurally identical. The present invention finally relates to hybrids or complexes which may be used on such supports.

The expression biochip is understood to mean a chip having at its surface a plurality of recognition zones, that is to say at least one hundred recognition zones, endowed with molecules having recognition properties. In the remainder of the text, and by a misuse of terminology, the term biochip is used independently of whether the chip is intended for chemical or biological analysis. The concept of biochip, more precisely of DNA chip, dates from the beginning of the 1990s. Nowadays, this concept has been extended since protein chips have started to be developed. It is based on a multidisciplinary technology incorporating microelectronics, nucleic acid chemistry, image analysis and computing. The principle of operation is based on a molecular biology foundation: the phenomenon of hybridization, that is to say the pairing by base complementarity of two DNA and/or RNA sequences.

The biochip method is based on the use of probes (DNA sequences representing a portion of a gene or an oligonucleotide), attached to a solid support on which a sample of nucleic acids labeled directly or indirectly with fluorochromes is caused to act.

However, it is quite possible to use other more conventional supports such as Petri dishes, microtiter plates which contain a number of separate wells, and the like. The expression support is understood to mean an analytical surface which contains only a few recognition zones, generally at most one hundred recognition zones. Each recognition zone comprises at least one molecule having recognition properties In all cases, the probes, also called recognition molecules, are positioned in a specific manner on the support or chip and each hybridization gives information on each gene represented. This information is cumulative, and makes it possible to detect the presence of a gene or to quantify the level of expression of this gene in the tissue studied. After hybridization, the support or chip is washed, read for example by a scanner and the analysis of the fluorescence is processed by a computer.

The support or chip which serves to attach the probes generally consists of a flat or porous surface composed of materials, such as:
- glass, an inexpensive, inert and mechanically stable material; the surface may be covered with a Teflon screen which delimits hydrophilic and hydrophobic zones,
- polymers,
- silicon, and
- metals, in particular gold and platinum.

However, it is also possible to use particles, for example magnetic particles, as described in patent applications WO-A-97/34909, WO-A-97/45202, WO-A-98/47000 and WO-A-99/35500 from one of the applicants.

To attach the probes (or recognition molecules), three main types of manufacture are distinguishable.

There is first of all a first technique which consists in depositing presynthesized probes. The attachment of the probes occurs by direct transfer, by means of micropipettes, microtips or by an ink-jet type device. This technique allows the attachment of probes having a size ranging from a few bases (5 to 10) up to relatively large sizes of 60 bases (imprinting) to a few hundreds of bases (microdeposition):

Imprinting is an adaptation of the method used by ink-jet printers. It is based on the propelling of very small spheres of fluid (volume<1 nl) and at a rhythm which may be up to 4000 drops/second. Imprinting does not involve any contact between the system releasing the fluid and the surface on which it is deposited.

Microdeposition consists in attaching probes which are a few tenths to a few hundredths of bases long to the surface of a glass slide. These probes are generally extracted from databases and exist in the form of amplified and purified products. This technique makes it possible to prepare chips called microarrays carrying about ten thousand spots, called recognition zones, of DNA on a surface of slightly less than 4 $cm^2$. There should however not be forgotten the use of Nylon membranes, called "macroarrays", which carry products which have been amplified, generally by PCR, with a diameter of 0.5 to 1 mm and the maximum density of which is 25 spots/$cm^2$. This highly flexible technique is used by many laboratories. In the present invention, the latter technique is considered as forming part of biochips. It is possible however to deposit, at the bottom of a microtiter plate, a certain volume of sample into each well, as is the case in patent applications WO-A-00/71750 under priority of 20 May and of 6 Dec. 1999 and FR00/14896 of 17 Nov. 2000 from one of the applicants, or to deposit, at the bottom of the same Petri dish, a certain number of drops separated from each other, according to another patent application FR00/14691 of 15 Nov. 2000 from this same applicant.

The second technique for attaching probes to the support or chip is called in situ synthesis. This technique results in the production of short probes directly at the surface of the chip. It is based on the synthesis of oligonucleotides in situ, invented by Edwin Southern, and is based on the method of oligonucleotide synthesizers. It consists in moving a reaction chamber, where the oligonucleotide extension reaction is taking place, along the surface of glass.

Finally, the third technique is called photolithography, which is a method at the origin of the biochips developed by Affymetrix. It also involves an in situ synthesis. Photolithography is derived from microprocessor techniques. The surface of the chip is modified by the attachment of photolabile chemical groups which can be activated by light. Once illuminated, these groups are capable of reacting with the 3' end of an oligonucleotide. By protecting this surface with masks of defined shapes, it is possible to illuminate and therefore activate selectively zones of the chip where it is desired to attach either of the four nucleotides. The successive use of different masks makes it possible to alternate protection/reaction cycles and therefore to produce the oligonucleotide probes on spots of about a few tenths of a square micrometer ($\mu m^2$). This resolution makes it possible to create up to several hundreds of thousands of spots on a surface of a few square centimeters ($cm^2$). Photolithography has advantages: massively parallel, it makes it possible to create a chip of N mers in only 4×N cycles.

All these techniques can of course be used with the present invention.

Methods using such supports or biochips can be essentially used for:
- searching for the presence or absence of a pathogenic agent, for example for a bacterium in meat,
- searching for the presence or absence of mutations. Knowing the molecular structure of the gene, oligonucleotides are manufactured which represent all or the complementary part of this gene. In the presence of the biological sample, hybridization will occur between all or part of said gene, which is generally labeled, for example by fluorescence, and the oligonucleotides, and the image obtained by fluorescence makes it possible to know if there is a mutation and in which position it is situated. In this application, the use of DNA chips is equivalent to sequencing for a diagnosis of mutation, with a huge advantage in terms of speed, and
- measuring the level of expression of genes in a tissue. The chip network carries a very large number of probes which correspond to all the genes of the species to be studied. A sample, for example of previously amplified mRNAs, which represents the active genes of the tissue, is hybridized. Fluorescence analysis makes it possible to know the level of expression of each gene.

The efficiency of such supports and biochips was tested on well known biological systems such as yeast (cell cycle, respiratory metabolism, fermentation and the like). Comparison of the results obtained by the chips with those previously obtained by other approaches showed agreement for the genes whose expression was already well known in these biological systems. This work has thus made it possible to validate the technology of biochips in relation to the more conventional supports which we have mentioned.

Moreover, companies are involved in novel methods which also allow genomic analyses to be performed in parallel. Thus, the microbead technique makes it possible to attach probes to microspheres carrying an individual "tag" or mark, and more precisely a genetic code. After reaction, the reading of this mark makes it possible to unambiguously identify a microbead and therefore the probe present at its surface. The microspheres are brought into contact with the test sample labeled with one or more fluorochromes. The mixture is then analyzed by flow cytometry which will, on the one hand, identify each bead according to its "tag", and, on the other hand, measure the fluorescence indicating an effective hybridization reaction.

DNA chips have paved the way to a novel instrumentation in molecular biology which can even incorporate various stages of analyses in miniaturized form, see in this regard patent applications WO-A-00/78452 under priority of 22 Jun. 1999 and FR00/10978 filed on 28 Aug. 2000 from one of the applicants. Furthermore, as already indicated above, the very high interest recently created by proteomics, the key post-genomics discipline, is accompanied by the emergence of the concept of protein chips. These also form part of the supports according to the invention.

The recognition molecules may be, for example, oligonucleotides, polynucleotides, proteins such as antibodies or peptides, lectins or any other ligand-receptor type system. In particular, the recognition molecules may contain DNA or RNA fragments.

When the support is brought into contact with a sample to be analyzed, the recognition molecules are capable of interacting, for example by hybridization in the case where they are nucleic acids or by formation of a complex in the case where they are antibodies or antigens, with target molecules present in a liquid biological sample.

Thus, by equipping a biochip with a plurality of recognition zones with various different recognition molecules, where each recognition molecule is specific for a target molecule, it is possible to detect and possibly quantify a large variety of molecules contained in the sample. It is of course obvious that each recognition zone contains only one type of recognition molecules which are identical to each other.

The support-recognition molecule-target molecule assembly can be detected by a detection molecule. The support-recognition molecule-target molecule-detection molecule assembly constitutes a test in a sandwich format. Tests in a sandwich format are widely used in diagnosis, whether in molecular diagnosis, ELOSA (Enzyme-Linked Oligo-Sorbent Assay) test for example, or in immunological diagnosis, for example ELISA (Enzyme-Linked Immuno-Sorbent Assay) test for example. In general, they comprise a recognition molecule, such as a nucleic acid probe or an antigen (case of an antigen sandwich) or an antibody (case of an antibody sandwich), which serves to capture a target, which will consist respectively of a nucleic acid probe or an antibody or an antigen. This recognition molecule is attached to a solid support in a manner known to a person skilled in the art, for example:
- either by adsorption,
- or by direct coupling,
- or via an intermediate protein, such as for example avidin or protein A,
- or via polymers.

The recognition molecule and target molecule assembly is then detected by a detection molecule, which will respectively consist of a nucleic acid probe or an antibody or an antigen. This detection molecule carries or may be subsequently combined with a marker, which marker is necessary in order to allow detection and/or quantification. The detection molecule, whether still combined with a marker or not, will still be called detection molecule.

In the text which follows, the term "hybridization" will be associated with the attachment of a nucleic acid to another nucleic acid, whereas the term "complexing" will be associated with the attachment of an antibody to an antigen. On the other hand, the term "attachment" will have a broader definition which may relate at the same time to:
- the attachment of a nucleic acid to another nucleic acid,
- the attachment of an antibody to an antigen, or
- the attachment of a biological molecule to a support.

The tests currently available are tests such as those developed by one of the applicants for immunological assays or the DNA chips developed by the company Affymetrix ("Accessing Genetic Information with High-Density DNA arrays", M. Shee et al., Science, 274, 610-614. "Light-generated oligonucleotide arrays for rapide DNA sequence analysis", A. Caviani Pease et al., Proc. Natl. Acad. Sci. USA, 1994, 91, 5022-5026), for medical diagnosis. In this technology, the capture probes are generally of small sizes, of around twenty nucleotides.

In the ELOSA field, that is to say in the field of detection of nucleic acids, see in this regard the patent application filed by one of the applicants WO-A-91/19812, there are defined in the same manner a capture oligonucleotide (recognition molecule), a target nucleic acid (target molecule) which is either DNA or RNA, and a detection oligonucleotide (detection molecule). Capture and detection oligonucleotides are complementary to part of the target but at the level of the regions of the target which are respectively structurally and physically different, such that the capture and detection oligonucleotides cannot hybridize to one another.

Whether in molecular diagnosis or in immunological assays, the detection elements carry a marker which allows the detection and/or the quantification of the target. The expressing labeling is understood to mean the attachment of a marker capable of directly or indirectly generating a detectable signal. Various markers have been developed with the permanent objective of improving sensitivity. They may be either radioactive, enzymatic, fluorescent, or, as described more recently, in the form of nanoparticles. These nanoparticles are different from microparticles, in particular in their size which remains considerably less than a micron. Because they are less trivial, they will be the subject of a more detailed disclosure later.

A nonlimiting list of these markers, which makes it possible to carry out imaging with a single marker, will be described in the remainder of the description.

Indirect systems may also be used, such as for example ligands capable of reacting with an antiligand. The ligand/antiligand pairs are well known to a person skilled in the art, which is the case for example of the following pairs:

biotin/streptavidin,
hapten/antibody,
antigen/antibody,
peptide/antibody,
sugar/lectin,
polynucleotide/complementary to the polynucleotide,
successive histidine sequence, called "tag", for a metal, for example nickel.

In this case, it is the ligand which carries the linking agent. The antiligand may be detectable directly by the markers described in the preceding paragraph or may itself be detectable by a ligand/antiligand.

These indirect detection systems can lead, under certain conditions, to a signal amplification. This signal amplification technique is well known to a person skilled in the art, and reference may be made to previous patent applications FR98/10084 or WO-A-95/08000 from one of the applicants or to the article J. Histochem. Cytochem. 45: 481-491, 1997.

Moreover, the applicants have jointly filed a patent application PCT/FROO/03359 under French priority of 2 Dec. 1999 on a signal amplification technique. However, the latter does not function on the basis of the teachings drawn from the preceding documents, which increase the number of markers at the level of the sites of attachment of said markers, but rather uses a particular coating at the surface of the support, which coating is based on a thin layer of a material chosen from silicon nitride, silicon carbide, titanium oxides, aluminum oxide, $ZrO_2$, $ZrO_4Ti$, $HfO_2$, $Y_2O_3$, diamond, MgO, oxynitrides ($Si_xO_yN_z$), fluorinated materials, $YF_3$, $MgF_2$. These two techniques may be cumulative.

As mentioned above, the markers may also be in the form of nanoparticles. The first experiments using conjugates with nanoparticles date back to 1980. They were motivated by the search for ultrasensitive labeling techniques which avoid the use of radioactivity or the use of enzymatic labelings which require not only time but also the use of toxic reagents. They have been widely developed and used since then and many types of particle have been developed, such as microparticles, nanoparticles of latex or particles of colloidal gold or alternatively fluorescent particles. In the text which follows, the term "particles" will be used without distinction for microparticles or nanoparticles or other particles of different sizes. Many particles are now commercially available (Bangs, Milteny, Molecular Probes, Polyscience, Immunicon).

Labeling experiments using nanoparticles were started in the field of immunological assays by J. H. W. Leuvering, P. J. H. M. Thal, M. Van der Waart and A. H. W. M. Schuurs, Sol Particle Immunoassay (SPIA). *Journal of Immunoassay* 1(1): 77-91, 1980.

The use of nanoparticles has allowed access to other technologies such as atomic force microscopy for reading immunological assays, with which technology, on a TSH detection model, a sandwich system mounted on a silicon support using anti-TSH detection antibody conjugates bound to gold nanoparticles has made it possible to obtain a sensitivity of the order of 1 pM. On this subject, reference may be made to the following two publications:

Agnès Perrin, Alain Theretz, and Bernard Mandrand Thyroïd stimulating hormone assays based on the detection of gold conjugates by scanning force microscopy. *Analytical biochemistry* 256:200-206, 1998, and Agnès Perrin, Alain Theretz, Véronique Lanet, S. Vialle, and Bernard Mandrand Immunomagnetic concentration of antigens and detection based on a scanning force microscopic immunoassay. *Journal of immunological methods* 8313, 1999

The use of nanoparticles for the detection of nucleic acids has been observed since only very recently. The work carried out in the field of immunology finds its equivalent in the field of nucleic acids. There is no fundamental innovation either in the labeling methods or in the detection methods. Since the ELISA plate no longer exists, it is indeed replaced by a flat support. The nanoparticles are then detected by microscopy, by amplification for surface plasmon resonance, called "biosensor" technique, or by measurement using AFM. Overall, the biological models remain simple models.

The work by Taton, T. A., Mirkin C. A. and Letsinger R. L. relating to: "Scanometric DNA array detection with nanoparticle probes" Science 2000 Sep. 8; 289(5485):1757-60, presents the use of gold nanoparticles coupled to detection oligonucleotides of 15 bases for detecting a target of 27 bases which is captured on a probe of 12 bases. The detection signal is amplified by labeling with silver. For high target concentrations of the order of 10 nanoMolar (nM), the detection of the particles is carried out by eye by observing the passage of a pink color. For the lowest concentrations, 100 picoMolar (pM) for example, the detection requires the use of a scanner. The sensitivity reached is of the order of 50 femtoMolar (fM). The authors are capable of dissociating the nanoparticles from the surface by heating, which tends to show the specificity of their labeling. However, according to the experiment of the applicants and because of the respective sizes of the detection oligonucleotides (15 bases), of the target oligonucleotides (27 bases) and of the capture oligonucleotides (12 bases), there must necessarily be dissociation between said nanoparticles and the detection oligonucleotides. This work is based, in addition, on a set of experiments which have been the subject of several publications (1996; 1997; 1997; 2000) and several patent applications and patents, such as WO-A-98/04740.

These researchers carry out a dissociation of the nanoparticles which does not distinguish the nanoparticles combined with a detection molecule with no mismatch with the target and the nanoparticles combined with a detection molecule with a mismatch with said target. In the text that follows, the expression "dissociation" is understood to mean in particular the separation between the recognition molecule and the target molecule and/or the separation of the target molecule and the detection molecule. If this dissociation is thermal, the physical characteristic involved consists of the melting point (Tm) which corresponds to the temperature zone where the DNA or RNA molecules are denatured. More precisely, this temperature corresponds to a state where a population of identical oligonucleotides, in the presence of an identical quantity of complementary oligonucleotides, is 50% in double-stranded form, that is to say paired, and 50% in single-stranded form.

While labelings with nanoparticles make it possible to obtain good sensitivity, there is nevertheless a compromise to be made between the increase in the specific signal and the decrease in the nonspecific signal. The nonspecific signal is of course limiting for improving the sensitivity and the dynamics of the method. The authors solve these problems by optimizing the experimental conditions. As a guide, some authors (Okano et al.; Anal. Biochem. 202:120-125; 1992) have optimized the concentration of detection oligonucleotides per particle, on the one hand, and the concentration of particles in the solution, on the other hand. They have also succeeded in reducing the nonspecific by adding BSA (bovine serum albumin).

As regards the use of nanoparticles for amplifying a signal obtained on a biosensor, reference is made to the work of Lin He, Michael D. Musick, Scheila R. Nicewaener, Franck G. Salinas, Stephen J. Benkovic, Michael J. Natan, and Christine D. Keating. Colloidal Au-enhanced surface plasmon resonance for ultrasensitive detection of DNA hybridization. *J. Am. Chem. Soc.* 122:9071-9077, 2000. Detection oligonucleotides (12 bases) conjugated with nanoparticles of colloidal gold are used to amplify the detection of a small sized nucleic acid target (24 mers) by surface plasmon resonance. They obtained a sensitivity of 10 pM, that is to say a surface density of $8.10^8$ molecules/cm$^2$ with an improvement in signal intensity of a factor of 100000. They verified the hybridization specificity by dissociating the nanoparticles from the surface either by heating or by digesting with restriction enzymes if the restriction site is present on the hybridized sequence. In this case, the labeling is used to amplify the signal, and the dissociation serves to show that the labeling results from a specific hybridization.

It is a verification of hybridization. Either the nanoparticles are separated by heating, in which case the scenario described by Taton (2000) exists and there is no specificity in the removal of the marker, or the nanoparticles are separated by restriction enzymes, in this case the nanoparticles are removed, for example by washing, while remaining combined with all or part of the detection molecule and/or the hybrid. There is an oriented character of this separation, but without dissociation or with a partial dissociation of the double strands.

Among the state of the art methods using nanoparticles, the document by Kubitschko S., Spinke J., Bruckner T., Pohl S. and Oranth N. "Sensitivity enhancement of optical immunosensors with nanoparticles." Anal. Biochem. 253(1):112-122 from 1997 evokes, in immunological diagnosis, the dissociation of the antibody conjugates in relation to the antigens. This dissociation is achieved with formic acid which serves to regenerate a microcomponent which still contains the antibodies for subsequent uses of the microcomponent.

It is more a method of cleaning a microcomponent; as a result, no de facto discrimination is made when the dissociation of the antibody conjugates is carried out in relation to the antigens which may be combined with the nanoparticles.

U.S. Pat. No. 6,093,370 provides another method which has the objective of recovering a DNA captured on a DNA chip. It is a photothermal dissociation carried out with an infrared (IR) laser at 1053 nanometers (nm) which irradiates with a power of between 10 and 100 mW the region of the chip on which it is desired to recover the DNA. The DNA redissolved in solution is amplified by PCR. The authors show that they are capable of extracting at least one DNA molecule per 169 nm$^2$, that is 10-17 mol/1000 μm$^2$.

However, they do not use a physicochemical dissociation for determining the hybridizations which are real because they are specific (true positives) from the other hybridizations.

In addition to the dissociation techniques mentioned above, that is to say by thermal denaturation (heating), by photothermal denaturation (IR laser), by digestion (restriction enzymes), by chemistry (formic acid), other methods of dissociating nucleic acids exist in the state of the art.

Thus, it is possible to modify the ionic strength of the hybridization buffer in order to dissociate the detection oligonucleotide from the target. Indeed, the melting point of the oligonucleotides varies according to the ionic strength of the buffer. The lower the ionic strength of the buffer, the less stable the oligonucleotide. It is also possible to combine the action of temperature with the buffer conditions.

It is also possible to use PNA (Peptide Nucleic Acid) or any other molecules used in the state of the art for capturing a nucleic acid. The PNA/oligonucleotide hybrids have the same thermal stability regardless of the ionic strength, that is to say that their melting point does not vary according to the ionic strength of the hybridization buffer. If the capture probe is a PNA and the detection probe is an oligonucleotide, on using a low ionic strength, the detection probe dissociates from the target whereas the target remains hybridized with the capture probe (PNA).

It is possible to chemically modify the detection probes in order to carry out the dissociation of the DNA under certain conditions. These dissociation methods do not relate to the particles which interact with the surface via the surface properties of the nanoparticles and of the support.

It is also possible to modify a base of the oligonucleotide, as described for example by Dreyer et al. (Proc. Natl. Acad. Sci., 82: 968-972; 1985). An EDTA group is coupled to a thymidine. In the presence of DTT, Fe(II) and $O_2$, a cleavage of the DNA occurs at the level of the thymidine carrying the EDTA.

As it is possible to couple a biotin to the detection oligonucleotide, for subsequent attachment to an avidin, it is also possible to couple a chemical group of the homobifunctional or heterobifunctional type (chemical functional groups necessary for its attachment to the oligonucleotide and to the support) which contains an additional chemical functional group which may be cleaved under certain conditions: for example a photocleavable group or alternatively a group reduced by DTT. In the case of a photocleavable group, exposing the oligonucleotide to a given wavelength cleaves the functional group and dissociates the oligonucleotide from its support.

Another method may also consist in adding a known sequence having a small size, called "tag", which has the property of forming a chelate with a chelating group present on the nanoparticle, via a metal ion. The tag may be a Histidine tag or any other molecule described by the state of the art. The chelating group may be an NTA (nitrilotriacetic acid) or any other group described by the state of the art. The dissociation will consist in using the methods described by the state of the art for dissociating the tag-metal-chelating group interaction (for example use of EDTA).

The dissociation may also be performed by displacing the detection probe, present on the nanoparticle, by oligonucleotides having identical sequences. These oligonucleotides may have either a shorter sequence or the same sequence with an additional sequence complementary to the target. Also, it is possible to use nucleic acid analogs for this displacement by competition, for example PNAs (Peptide Nucleic Acids) or another analog having the advantage of a neutral backbone.

As regards the dissociation of protein molecules such as antigens and/or antibodies, it is possible to apply any of the methods described in the state of the art for dissociating the interactions between an antigen and an antibody (numerous techniques known in the field of affinity chromatography). By way of example, it is thus possible to carry out the dissociation by applying acid solutions such as a glycine buffer at acidic pH or solutions with high ionic strength such as 5M LiCl (Kubitschko et al., Anal. Biochem. 253(1):112-122; 1997). It is also possible to use denaturing agents such as guanidium chloride, urea or alternatively solutions containing detergents; or methods for digesting proteins with proteases or even endoproteases specific for the antigen or the antibody or alternatively nonspecific for the antigens or the antibodies.

In the case of a double labeling, the dissociation should be oriented, without being denaturing for the proteins so as to allow a second labeling. This may be carried out for example by displacement by the use of synthetic peptides, whose sequence corresponds to the sequence of the epitopes of monoclonal antibodies but with a higher affinity.

It is also possible to modify, chemically or by genetic engineering techniques, antigens and antibodies in order to carry out the dissociation under certain conditions. These methods do not relate, however, to the protein molecules which interact directly with the surface in a nonspecific manner. Thus, the modification may relate to one of the proteins (antigen or antibody) by inserting, for example by genetic engineering, a sequence for cleavage by an endoprotease. In the presence of the enzyme, there is cleavage of the protein to be detected. The second labeling is performed using a second monoclonal antibody specific for the remaining protein sequence. The modification may relate to the end of the protein by adding, for example by genetic engineering, a tag. This tag may be recognized by monoclonal antibodies, the dissociation is then made by displacement using competitor peptides or antibodies. As a guide, the tag added may be a "poly-Histidine" sequence, may contain a sequence for cleavage by endoproteases which does not exist in the sequence, the dissociation is then carried out by enzymatic cleavage. Other sequences such as protein "splice" sequences may also be integrated into the protein. The cleavage is made in the presence of DTT for example.

Finally, it is also possible to add to the detection protein a nucleic acid sequence. A tag is then obtained, as above, which can be recognized by a nucleic probe which is itself conjugated with a nanoparticle. The dissociation, oriented or otherwise, can then be carried out by one of the techniques described for nucleic acids, provided that the protein assembly is not denatured in the case of an oriented dissociation. Competition methods are advantageous from this point of view.

All these elements mentioned above are capable of being incorporated into the invention in order to further improve the performance thereof.

According to patent application WO-A-99/65926, from one of the applicants, it is also possible to dispense with the detection molecule proper in the case of nucleic acids. Each target can be cleaved chemically, enzymatically or physically, while undergoing simultaneous labeling or otherwise. The presence of a detection molecule is then no longer necessary since the target molecule is labeled, see in particular patent application PCT/FR99/01469.

Devices exist for reading molecules which are labeled or otherwise, and which may be present in the recognition zones of the chip.

The reading of the recognition zones may indeed also be carried out without the presence of the marker, such a technology already being known in the state of the art. The applicants have in fact jointly filed a patent application PCT/FR00/02703 under French priority of 30 Sep. 1999 on such a reading technique, which uses a photothermal method.

Among the direct methods for detection of hybridization, it is possible to distinguish in particular the detection of the variation in mass, of the variation in thickness and of the variation in index. Photothermal methods are also known which are described in the document by S. E. Bialkowski, vol. 137, under the title: "Photothermal spectrocopy methods for chemical analysis" taken from Chemical analysis: a series of monographs on analytical chemistry and its application, Wiley. Finally, the document U.S. Pat. No. 4,299,494 describes a technique for photothermal deflection.

Thus, the invention finds applications in the fields of biological and chemical analysis.

In general, the reading of the molecular or immunological diagnosis mentioned above has the main disadvantage of being limited by false-positives, that is to say hybrids or complexes which form when they should not have hybridized or formed a complex, and/or false-negatives, that is to say hybrids or complexes which do not form when they should have hybridized or formed a complex. This presence of false-positives or of false-negatives causes another disadvantage, which is the consequence of the first disadvantage mentioned above; the molecular diagnosis or the immunological assays lack sensitivity (power to identify the hybrid or the complex sought when it is present in a small quantity in a biological sample to be tested) and/or specificity (power to detect the hybrid or the complex sought in the biological sample to be tested containing other hybrids or complexes). This can cause diagnostic errors which are not acceptable for patients, practitioners and the companies manufacturing such tests.

The present invention proposes to solve all the disadvantages of the prior art mentioned above by providing a method of reading which is little or not influenced by the presence of false-positives and which therefore very substantially improves the sensitivity and specificity of diagnostic tests.

To this effect, the present invention relates, according to a first embodiment, to a method of reading on a support at least one biological reaction, which consists in:
bringing the support into contact with at least a first liquid sample containing at least one group of biological recognition molecules, which are identical to each other, so as to attach these recognition molecules to the support, preferably at the level of a recognition zone,
bringing the functionalized support into contact with at least a second liquid sample containing at least one labeled target biological molecule so as to attach this or these target molecule(s) to said recognition molecule(s),
producing a first image of said support after this attachment of the labeled target molecule(s),
treating the support under physicochemical conditions allowing the separation of each target molecule with respect to a recognition molecule to which it is specifically attached,
producing a second image of said support after this separation, and
analyzing the two images in order to determine the specific attachments between the recognition and target molecule(s).

According to a second embodiment, the present invention relates to a method of reading on a support at least one biological reaction, which consists in:

bringing at least a first liquid sample containing at least one group of biological recognition molecules, which are identical to each other, into contact with at least a second liquid sample containing at least one labeled target biological molecule so as to attach this or these target molecule(s) to said recognition molecule(s), bringing the support into contact with the mixture of the at least two first and second liquid samples containing at least the group of biological recognition molecules optionally complexed with at least one target molecule so as to attach this or these recognition molecules or complex(es) to the support, preferably at the level of a recognition zone, producing a first image of said support after this attachment of the labeled target molecule(s), treating the support under physicochemical conditions allowing the separation of each target molecule with respect to a recognition molecule to which it is specifically attached, producing a second image of said support after this separation, and analyzing the two images in order to determine the specific attachments between the recognition and target molecule(s).

In the preceding two cases, the method may additionally comprise the following additional subsequent steps:

bringing the functionalized and treated support, after specific separation, into contact with the second liquid sample or with another liquid sample so as to again attach at least one labeled target biological molecule to:
the biological recognition molecule(s) from which it or they had been separated, and/or
any other recognition molecule(s) derived from the same recognition zone, producing a third image of said support after this new attachment of target molecule(s), analyzing the third image with respect to the preceding analysis of the two first images in order to confirm the specific attachments between the recognition and target molecule(s).

According to a third embodiment, the present invention relates to a method of reading on a support at least one biological reaction, which consists in:

bringing the support into contact with at least a first liquid sample containing at least one group of biological recognition molecules, which are identical to each other, so as to attach these identical recognition molecules to the support, preferably at the level of a recognition zone, bringing the functionalized support into contact with at least a second liquid sample containing at least one biological target molecule so as to attach this or these target molecule(s) to said recognition molecule(s), bringing the functionalized and treated support into contact with at least a third liquid sample containing at least one labeled detection molecule so as to attach this or these detection molecule(s) to said target molecule(s) attached to the recognition molecule(s), producing a first image of said support after this attachment of the labeled detection molecule(s), treating the support under physicochemical conditions allowing the separation of each detection molecule with respect to a target molecule to which it is specifically attached, producing a second image of said support after this separation, and analyzing the two images in order to determine the specific attachments between the target and detection molecule(s).

According to a fourth embodiment, the present invention relates to a method of reading on a support at least one biological reaction, which consists in:

bringing at least a first liquid sample containing at least one group of biological recognition molecules, which are identical to each other, into contact with at least a second liquid sample containing at least one biological target molecule so as to attach this or these target molecule(s) to said recognition molecule(s), bringing the support into contact with the mixture of the at least two first and second liquid samples containing at least one group of identical biological recognition molecules, which recognition molecule(s) is (are) optionally complexed with at least one target molecule, so as to attach this or these recognition molecule(s) and/or complex(es) to the support, preferably at the level of a recognition zone, bringing the functionalized and treated support into contact with at least a third liquid sample containing at least one labeled detection molecule so as to attach this or these detection molecule(s) to said target molecule(s) attached to the recognition molecule(s), producing a first image of said support after this attachment of the labeled detection molecule(s), treating the support under physicochemical conditions allowing the separation of each detection molecule with respect to a target molecule to which it is specifically attached, producing a second image of said support after this separation, and analyzing the two images in order to determine the specific attachments between the target and detection molecule(s).

According to a fifth embodiment, the present invention relates to a method of reading on a support at least one biological reaction, which consists in:

bringing at least a first liquid sample containing at least one group of biological recognition molecules, which are identical to each other, into contact with at least a second liquid sample containing at least one biological target molecule so as to attach this or these target molecule(s) to said recognition molecule(s), bringing the mixture of the two first and second liquid samples into contact with at least a third liquid sample containing at least one labeled detection molecule so as to attach this or these detection molecule(s) to said target molecule(s) attached to the recognition molecule(s), bringing the support into contact with the mixture of the at least three first, second and third liquid samples containing at least the group of identical biological recognition molecules, which recognition molecule(s) is (are) optionally complexed with at least one target molecule which is itself optionally complexed with at least one detection molecule so as to attach this or these recognition molecules or complex(es) to the support, preferably at the level of a recognition zone, producing a first image of said support after this attachment of the labeled detection molecule(s), treating the support under physicochemical conditions allowing the separation of each detection molecule with respect to a target molecule to which it is specifically attached, producing a second image of said support after this separation, and analyzing the two images in order to determine the specific attachments between the target and detection molecule(s).

According to a sixth embodiment, the present invention relates to a method of reading on a support at least one biological reaction, which consists in:

bringing at least a second liquid sample containing at least one target biological molecule into contact with at least a third liquid sample containing at least one biological detection molecule, so as to attach this or these target molecule(s) to the detection molecule(s), bringing the mixture of the two second and third liquid samples into contact with at least a first liquid sample containing at least one group of recognition molecules, which are identical to each other, so as to attach this or these recognition molecule(s) to said target molecule(s), optionally attached to said detection molecule(s), bringing the support into contact with the mixture of the at least three first, second and third liquid samples containing at least the group of identical biological recognition molecules, which recognition molecule(s) is (are) optionally complexed with at least one target molecule which is itself optionally complexed with at least one detection molecule so as to attach this or these recognition molecules or complex(es) to the support, preferably at the level of a recognition zone, producing a first image of said support after this attachment of the labeled detection molecule(s), treating the support under physicochemical conditions allowing the separation of each detection molecule with respect to a target molecule to which it is specifically attached, producing a second image of said support after this separation, and analyzing the two images in order to determine the specific attachments between the target and detection molecule(s).

According to a seventh embodiment, the present invention relates to a method of reading on a support at least one biological reaction, which consists in:

bringing the support into contact with at least a first liquid sample containing at least one group of biological recognition molecules, which are identical to each other, so as to attach these identical recognition molecules to the support, preferably at the level of a recognition zone, bringing at least a second liquid sample containing at least one target biological molecule into contact with at least a third liquid sample containing at least one biological detection molecule, so as to attach this or these target molecule(s) to the detection molecule(s), bringing the mixture of the at least two second and third liquid samples containing at least one optionally complexed target molecule into contact with a detection molecule so as to attach this or these target molecule(s) to said recognition molecule(s), producing a first image of said support after this attachment of the labeled detection molecule(s), treating the support under physicochemical conditions allowing the separation of each detection molecule with respect to a target molecule to which it is specifically attached, producing a second image of said support after this separation, and analyzing the two images in order to determine the specific attachments between the target and detection molecule(s).

According to an eighth embodiment, the present invention relates to a method of reading on a support at least one biological reaction, which consists in:

bringing at least a second liquid sample containing at least one target biological molecule into contact with at least a third liquid sample containing at least one biological detection molecule, so as to attach this or these target molecule(s) to the detection molecule(s), bringing at least a first liquid sample containing at least one group of biological recognition molecules, which are identical to each other, into contact with the mixture of the at least two second and third liquid samples containing at least one target molecule optionally complexed with a detection molecule so as to attach this or these target molecule(s) to said recognition molecule(s), bringing the support into contact with the mixture of the at least three first, second and third liquid samples containing at least one group of biological recognition molecules, which are identical to each other, which recognition molecule(s) is (are) optionally complexed with at least one target molecule, which is itself optionally complexed with a detection molecule, so as to attach these identical recognition molecules to the support, preferably at the level of a recognition zone, producing a first image of said support after this attachment of the labeled detection molecule(s), treating the support under physicochemical conditions allowing the separation of each detection molecule with respect to a target molecule to which it is specifically attached, producing a second image of said support after this separation, and analyzing the two images in order to determine the specific attachments between the target and detection molecule(s).

In the preceding five cases, the method may comprise the following additional subsequent steps:

bringing the functionalized and treated support, after specific separation, into contact with the third liquid sample or with another liquid sample, so as to again attach at least one labeled detection molecule to:

the target molecule(s) from which it or they had been separated, and/or any other target molecule(s) (3) attached to one or more of the recognition molecules (2) derived from the same recognition zone, producing a third image of said support after this new attachment of detection molecule(s), analyzing the third image with respect to the preceding analysis of the two first images in order to confirm the specific attachments between the target and detection molecule(s).

According to a first variant embodiment of the invention, at least one washing is carried out after attachment:

of the recognition molecules to the support, the recognition molecules being optionally attached to labeled target molecules and/or to nonlabeled target molecules, the latter being optionally attached to detection molecules, and/or of the labeled target molecules and/or of the nonlabeled target molecules to the recognition molecules, which are themselves attached beforehand to said support, the target molecules being optionally attached to detection molecules, and/or of the detection molecules to nonlabeled target molecules, the latter being attached to recognition molecules, which are themselves attached to the support.

According to a second variant embodiment of said invention, the support consists of magnetic particles, and the method comprises steps of magnetizing said magnetic particles, which are preferably put in place:

during any step(s) of physicochemical treatment and/or of producing an image, as described above, and/or before any washing step, as described above.

According to a third variant embodiment of the invention, the bringing of the support into contact with at least two different first liquid samples, optionally mixed beforehand, allows the attachment of at least two different recognition molecules to said support in at least two distinct recognition zones.

Regardless of the variant, when it is desired to quantify at least two optionally different target molecules, the detection molecule consists of a molecule combined directly or indirectly with at least one marker, such as a nanoparticle, whose means, which produce the images, allow individual visualization, despite the presence of other neighboring detection molecules and the like.

In all cases, the physicochemical conditions allowing the separation of the labeled target molecules with respect to the recognition molecules or of the detection molecules with respect to the target molecules may be obtained by heating to a melting point.

According to a preferred embodiment, the labeled target molecules, the recognition molecules or the target molecules consist of or the detection molecules comprise nucleic acids.

According to another preferred embodiment, the labeled target molecules, the recognition molecules or the target molecules consist of or the detection molecules comprise antibodies and/or antigens.

Whatever the case, the labeling of the target molecules or of the detection molecules may be carried out by:

particles which can be visualized by conventional optical microscopy, fluorescence microscopy, dark field microscopy or atomic force microscopy, molecules which can be visualized by atomic force microscopy, enzymes with precipitating product which produce a detectable signal, for example by fluorescence, luminescence, such as horseradish peroxidase, alkaline phosphatase, β-galactosidase or glucose-6-phosphate dehydrogenase, chromophores such as fluorescent or luminescent compounds, electronic markers which can be detected by electron microscopy, absorbent molecules which can be visualized by thermal lens microscopy.

In the case where three successive images of the support are produced, the other liquid sample, in place either of the second or of the third liquid sample, for bringing into contact the functionalized and treated support, after specific separation, comprises a different marker from that contained in said second or third liquid sample.

The present invention also relates to a hybrid or complex obtained during the implementation of the method disclosed above, which is bound to a support by a recognition molecule, the hybrid or complex consisting of the recognition molecule bound to a target molecule which is itself bound to a detection molecule. In this case, the bond between the detection molecule and the target molecule is easier to dissociate under suitable physicochemical conditions than the bond between said target molecule and the recognition molecule, and the bond between the target molecule and the recognition molecule is easier to dissociate under suitable physicochemical conditions than the bond between said recognition molecule and the support.

In this case, when the recognition, target and detection molecules are based on nucleic acids, the pairing between the detection molecule and the target molecule comprises fewer total paired bases and/or comprises fewer paired Guanine-Cytosine bases than the bond between the target molecule and the recognition molecule. Preferably, the number of total paired bases between the detection molecule and the target molecule is between five and fifty, preferably between ten and twenty five and still more preferably between twelve and twenty, and the number of total paired bases between the target molecule and the recognition molecule is between ten and one hundred, preferably between fifteen and fifty and more preferably still between twenty and thirty. Furthermore, the proportion of paired Guanine-Cytosine bases involved in the binding between the detection molecule and the target molecule is less than or equal to 50%, preferably less than or equal to 45%, and the proportion of paired Guanine-Cytosine bases involved in the binding between the target molecule and the recognition molecule is greater than or equal to 50%, preferably greater than or equal to 55%.

The present invention finally relates to a biochip consisting of a plurality of hybrids or complexes, as described above, attached to at least one support, as mentioned above.

On this biochip, the structurally identical hybrids or complexes are grouped together to form recognition zones.

The accompanying figures and examples are given by way of an explanatory example and do not imply any limitation. They will make it possible to better understand the invention.

Finally.

The examples above will also make it possible to better understand the invention.

EXAMPLE 1

Specific Dissociation of the Detection Molecules Combined with Magnetic Nanoparticles in Relation to Target Molecules The model, chosen from HIV sequences, consists of:

a recognition molecule 2, biotinylated in 5', to allow its attachment to a support 1, corresponding to the sequence set forth in SEQ ID NO: 1:5'-TCACTATTAT CTTG-TATTAC TACTGCCCCT TCACCTTTCC AGAG-GAGCTT TGCTGGTCCT TTCCAAAGTG-3' (length: 70 nucleotides), a target molecule 3, corresponding to the sequence set forth in SEQ ID NO: 2:

```
                                  5'-ACAGCAGTAC
AAATGGCAGT ATTCATCCAC AATTTTAAAA GAAAAGGGGG
GATTGGGGGG TACAGTGCAG GGGAAAGAAT AGTAGACATA
ATAGCAACAG ACATACAAAC TAAAGAATTA CAAAAACAAA
TTACAAAAAT TCAAAATTTT CGGGTTTATT ACAGGGACAG
CAGAAATCCA CTTTGGAAAG GACCAGCAAA GCTCCTCTGG
AAAGGTGAAG GGGCAGTAGT AATACAAGAT AATAGTGACA
TAAAAGTAGT GCCAAGAAGA AAAGCAAAGA TCATTAGGGA
TTATGGAAAA CAGATGGCAG GTGATGATTG TGTGGCAAGT
AGACAGGATG AGATTAGAAC ATGGAAAAGT TTAGTAAAAC
ACCATATGTA TGTTTCAGGG AAAGCTAGGG GATGGTTTTA
TAGACATCAC TATGAAAGCC CTCATCCAAG AATAAGTTCA
GAAGTAAATC GAATTCCCGC GGCCATGGCC GCCGGGAGCA
TGCGACGTCG GGCCCAATTC GCCC-3'
(length: 514 nucleotides), and
``` a detection molecule 4, comprising an oligonucleotide biotinylated at its 3' end, corresponding to the sequence set forth in SEQ ID NO: 3:5'-TTCTGAACTT ATTCTT-3' (length: 16 nucleotides), and a marker.

In SEQ ID NO:2, part of the sequence (nucleotides 179-248 of SEQ ID NO:2) is represented in bold and underlined, this part corresponds to the sequence complementary to SEQ ID NO:1 of the recognition molecule 2. Another part of the sequence (nucleotides 438-453 of SEQ ID NO:2) is represented solely underlined, this part corresponds to the sequence complementary to SEQ ID NO:3 of the detection molecule 4.

First Step: Immobilization of the Recognition Molecules on the Support:

The support 1 used is a Corning glass slide (reference 0211) format 18 mm×18 mm, silanized beforehand with 1% AMPMES (Amino-propyl-dimethyl-ethoxysilane).

Onto this support 1 is grafted neutravidin (Neutravidin biotin-binding Protein Pierce reference 31000AH) via PDC (Phenylene diisothiocyanate) at a concentration of 1 mg/ml of PBS (Phosphate Buffer Saline) in the form of a deposit of 2 μl, that is 2 mm in diameter. This preliminary step, not represented in the figures, allows subsequent attachment of the recognition molecules 2 to the support 1, by immobilization of the biotinylated end of said recognition molecules 2 to the neutravidin present on said support 1.

After washing with a solution of 1% aqueous ammonia, 1 M NaCl, 1% BSA (Bovine Serum Albumin) and incubating in this same buffer for 10 minutes, the support 1 is washed with water and then with TE buffer (10 mM Tris at pH 8, 1 mM EDTA), 1 M NaCl, in order to remove the neutravidin not attached.

The support 1 onto which the neutravidin is attached is then incubated for 20 minutes at room temperature in the presence of recognition molecules 2, in solution in TE, 1 M NaCl, at a concentration of 5 μm. The support 1 is washed in a solution of 1% aqueous ammonia, 1 M NaCl, 1% BSA by an incubation of 10 minutes. This support 1 is then immersed into this same solution so as to saturate the totality of the recognition zones, for 20 minutes, washed with water and then with TE, so as to promote the removal of the recognition molecules 2 not attached to the neutravidin.

Figure 1:
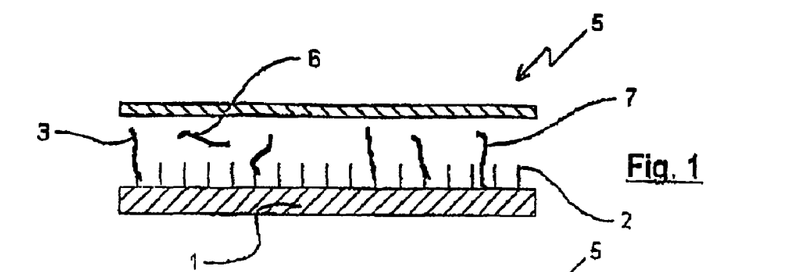
FIG. 1 represents a step of the method of reading consisting in the introduction of a second liquid containing target molecules into a biochip which carries, for its part, recognition molecules.

The step of attachment of the recognition molecules 2 to the support 1 via their biotinylated 5' end is not represented in the figures, since the support 1, according to FIG. 1, is already functionalized to receive the target molecules 3.

Second Step: Hybridization of the Target Molecules to the Recognition Molecules:

After immobilization of the recognition molecules 2, the hybridization thereof 2 with the target molecules 3 is carried out by incubation of the support in TE 1 M NaCl, 0.05% Triton X100 overnight at 35° C., which corresponds to FIG. 1. In the present case, 70 complementary base pairs are hybridized.

Figure 2:
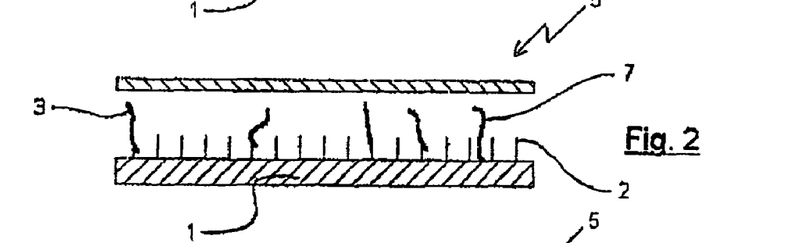
FIG. 2 represents a step of the method of reading consisting in a washing to remove the nonhybridized or noncomplexed target molecules, that is to say which are not attached within the biochip.

The support 1 is then taken up, washed in this same buffer for 15 minutes at room temperature, as represented in FIG. 2, which makes it possible to remove the target molecules 6 not hybridized.

It is interesting to note that according to one variant of the invention, the recognition molecules 2 may be hybridized beforehand with the target molecules 3 and the mixture is then brought into contact directly with the support 1.

Third Step: Labeling of the Oligonucleotides with Nanoparticles in Order to Synthesize the Detection Molecules:

To detect the target molecules 3 hybridized with the recognition molecules 2, detection molecules 4 are labeled beforehand with magnetic nanoparticles from Immunicon (Huntingdon Valley, USA; ref.: F3106). These nanoparticles have a diameter of 145 nm and are functionalized with streptavidin, generally 6000 to 20000 molecules of streptavidin are attached to a single nanoparticle, each streptavidin allowing the attachment of four biotins. These nanoparticles are incubated at a concentration of $10^9$ particles/ml at 4° C. overnight in TE buffer containing 1 M NaCl, 0.14 mg/ml salmon DNA, 0.05% Triton X100. The oligonucleotide, forming the basis of the detection molecule 4, biotinylated at one of its ends, is then added to the solution of nanoparticles, at the rate of one thousand detection oligonucleotides per nanoparticle, and then incubated for 30 minutes at 35° C. Each detection oligonucleotide combined with a nanoparticle constitutes a detection molecule 4.

Figure 3:
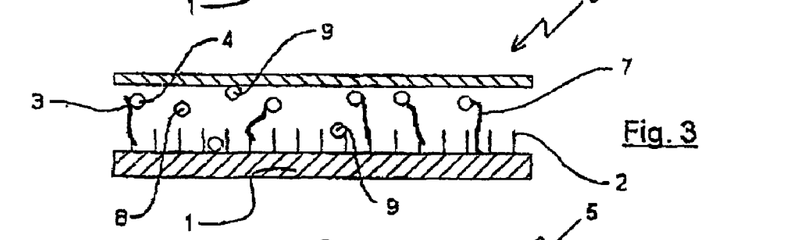
FIG. 3 represents a step of the method of reading consisting in the introduction of a third liquid containing detection molecules into a biochip which carries both recognition molecules and target molecules.

Fourth Step: 1st Hybridization of the Detection Molecules with the Target Molecules:

Each step, represented in FIG. 3, consists in bringing the target molecules 3 hybridized with the recognition molecules 2 into contact with the detection molecules 4. For this, the support 1, onto which are attached the target molecules 3 hybridized with the recognition molecules 2, is incubated with 1 ml of the solution of detection molecules 4, prepared according to the preceding step, at the rate of $10^9$ nanoparticles/ml for 1 hour at room temperature. The hybridization is performed on 16 complementary base pairs.

Figure 4:
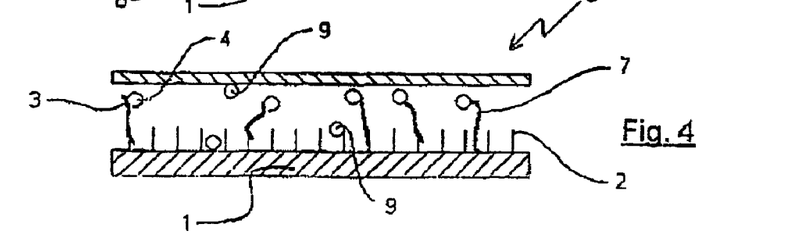
FIG. 4 represents a step of the method of reading consisting in a washing to remove the nonhybridized or noncomplexed detection molecules, that is to say which are not attached within the biochip.

The support 1 is then washed in TE buffer containing 1 M NaCl, 0.05% Triton X100 for 15 minutes at room temperature so as to promote the removal of the detection molecules not hybridized with the target molecules 3, as represented in FIG. 4.

It is advantageous to note that according to one variant of the invention, the detection molecules 4 may be hybridized beforehand with the target molecules 3 and the mixture is then directly brought into contact with the support 1 to which the recognition molecules 2 are attached.

Figures 5, 6:
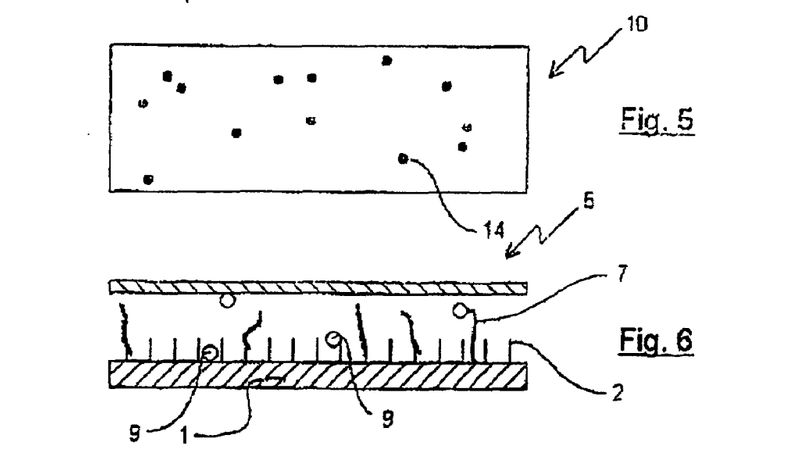
FIG. 5 represents a step of the method of reading consisting in producing a first image which represents the hybrids or complexes detected on the biochip after the steps represented in FIGS. 1 to 4 above.
FIG. 6 represents a step of the method of reading consisting in an oriented cleavage allowing dissociation between the target molecules and the detection molecules.

Fifth Step: Production of a 1st Image:

A first image 10 is produced by dark field microscopy (twenty (20) times magnification with a dark field lens) which makes it possible to visualize nonfluorescent small sized nanoparticles, which corresponds to FIG. 5.

Sixth Step: Thermal Dissociation of the Target Molecules and of the Detection Molecules:

This dissociation step is represented in FIG. 6. The detection molecule 4 possesses a melting point of 51° C. whereas the recognition molecule 2 has a measured melting point of 90.5° C. A temperature of 60° C. constitutes a temperature greater than the melting point of the detection molecule 4 and less than the melting point of the recognition molecule 2, allowing dissociation between the target molecule 3 and the detection molecule 4. The dissociation of the detection molecules 4 is thus performed by treating the support 1 in a TE buffer containing 0.05% Triton X100 at 60° C. for 1 hour. Some detection molecules 4 remain at the surface, but those which remain correspond to the detection molecules not specifically adsorbed at the surface.

This dissociation may also be obtained by incubating the support 1 in Sodium Phosphate buffer at pH 5.5 at a concentration of 100 mM, containing 1 mM EDTA, 0.05% Triton X100 for 1 hour at 60° C. The dissociation does not depend on the nature of the buffer used for the hybridization (Sodium Phosphate buffer at pH 5.5 and 100 mM, 1 M NaCl, 1 mM EDTA, 0.05% Triton X100, or Sodium Phosphate buffer at pH 5.5 and 100 mM, 0.1 M NaCl, 1 mM EDTA, 0.05% Triton X100). The conditions necessary are the use of a low ionic strength, or even salt-free, buffer and heating for 1 hour at 60° C.

Figure 7:
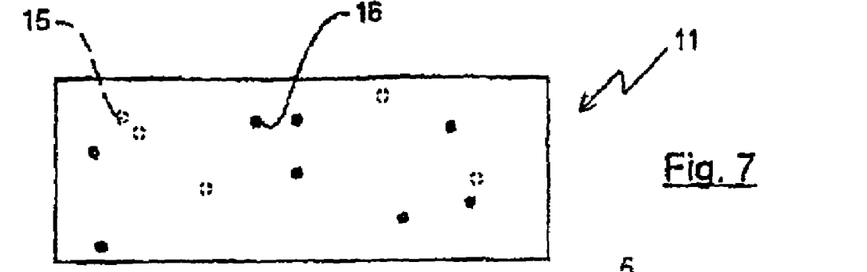
FIG. 7 represents a step of the method of reading consisting in the production of a second image which represents the hybrids or complexes detected on the biochip after the step represented in FIG. 6 above.

Seventh Step: Production of a Second Image:

There is produced by dark field microscopy a second image 11 which makes it possible to observe that most of the detection molecules 4 hybridized beforehand with the target molecules, which constituted true-positives, have disappeared. That is what is represented in FIG. 7.

This 2nd image 11 thus makes it possible to detect the detection molecules 4 which are only adsorbed at the surface or which were not properly hybridized with the target molecules 3, that is to say without mismatch, which constitute false-positives.

By subtracting the detection spots present on the 1st image 10 from those of the 2nd image 11, it is possible to thus distinguish the presence of true-positives and false-positives.

Eighth Step: 2nd Hybridization of the Detection Molecules with the Target Molecules:

With the aim of further refining the results of the preceding steps, the support 1 is incubated a second time with the detection molecules 4 under identical conditions to the first hybridization described above in the fourth step, so as to reconstitute the labeling of the target molecules 3, already hybridized with the recognition molecules 2, with the detection molecules 4. That is what is indeed represented in FIG. 8.

Figures 8, 9:
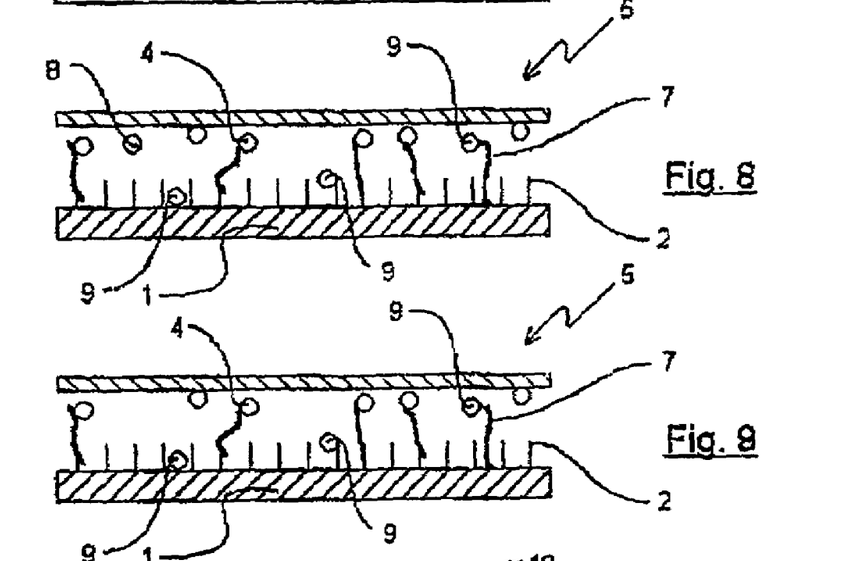
FIG. 8 represents a step of the method of reading consisting in the reintroduction of the third liquid containing detection molecules into a biochip which carries both recognition molecules and target molecules.
FIG. 9 represents a step of the method of reading consisting in a washing to remove the detection molecules which have not become attached within the biochip.

The support 1 is then washed in TE buffer containing 1 M NaCl, 0.05% Triton X100 for 15 minutes at room temperature, which corresponds to FIG. 9.

Figure 10:
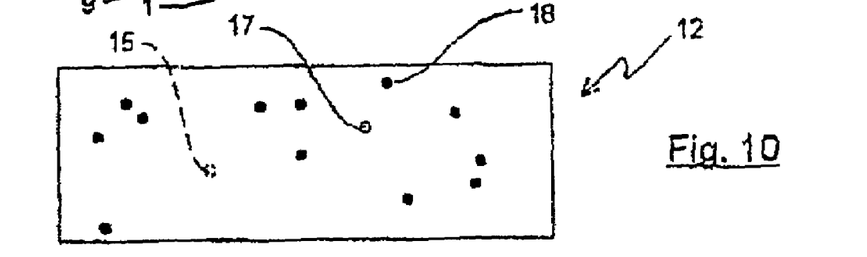
FIG. 10 represents a step of the method of reading consisting in producing a third image which represents the hybrids or complexes detected on the biochip after the step represented in FIGS. 8 and 9 above.

Ninth step: Production of a 3rd Image:

This 3rd image 12 makes it possible to refine the distinction made during the seventh step between the true-positives and the false-positives. Furthermore, the detection molecules 4 being specific for the target molecules 3, this 3rd image 12 makes it possible to verify, as represented in FIG. 10, that said target molecules 3 are still present on said recognition molecules 2, since the same intensity of the detection signal is obtained as that for the 1st image. Consequently, the target molecules 3 are not dissociated from the recognition molecules 2 during the treatment with TE containing Triton X100 at 60° C.: the dissociation is oriented.

Figure 11:
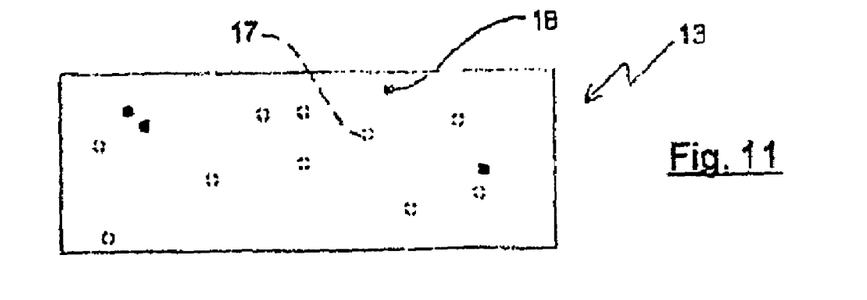
FIG. 11 represents the last step of the method of reading according to the invention, this step consists in the simultaneous analysis of the second and third images in order to obtain a fourth image which is truly representative of the hybrids or complexes detected on the biochip.

It is also possible to carry out a final step corresponding to FIG. 11, where computer means can process the three images obtained 10, 11 and 12 so as to precisely define the detection spots 18 really corresponding to detection molecules 4 hybridized with recognition molecule 2—target molecule 3 hybrids.

EXAMPLE 2

Oriented Dissociation of the Detection Molecules Combined with Fluorescent Nanoparticles in Relation to Target Molecules This example uses the biological model described in Example 1.

The two first steps described in Example 1, which correspond respectively to the immobilization of the recognition molecules 2 on the support 1, and the hybridization of the target molecules 3 with the recognition molecules 2 are performed in a comparable manner in this example.

The third step, which corresponds to the labeling of the detection molecules on the other hand differs from Example 1 since the nanoparticles which were used for labeling the detection molecules 4 are fluorescent nanoparticles supplied by Molecular Probe (Eugene Oreg. USA ref.: T8860) of 100 nm in diameter, already functionalized with neutravidin. The detection molecules 4 thus obtained are purified on Microcon YM30 (Amicon MILLIPORE ref.: 42409).

The 1st hybridization of the detection molecules 4 with the target molecules is carried out as described in the fourth step of Example 1.

The counting of the detection spots is carried out by means of a 1st image 10, obtained by fluorescence microscopy according to FIG. 5.

The dissociation step is carried out in TE buffer containing 0.05% Triton X100 at 60° C. for one hour, as represented in FIG. 7, as described above in the sixth step of Example 1.

A second image 11 is produced by fluorescence microscopy. By subtracting the intensity of fluorescence obtained in the first image from that obtained in the second image, it is possible to deduce therefrom the fluorescence intensity due to the presence of false-positives. In a comparable manner to what is described in Example 1, a 2nd hybridization of the detection molecules 4 with the target molecules 3 followed by a third image 12 makes it possible to check that a fluorescence intensity is indeed obtained which is comparable to that detected in the first image 10, demonstrating once again that the dissociation is indeed oriented.

The dissociation can therefore be performed with detection molecules 4 labeled with nanoparticles of a different nature.

EXAMPLE 3

Oriented Dissociation of a Target Molecule Hybridized Between Two Oligonucleotides Combined with Nanoparticles The sequences of the recognition molecules 2, target molecules 3 and detection molecules 4 used in this example are identical to those described in Example 1.

In this example, the invention is used with a double hybrid combining the target molecule 3 with:
the recognition molecule 2, itself 2 combined with a magnetic particle, and
the detection molecule 4 labeled with a fluorescent nanoparticle.

The use of a magnetic particle, which does not serve here as a marker, makes it possible to use a simple purification protocol by mere magnetization, and the use of a fluorescent particle makes it possible to use fluorescence as the sensitive method for detecting and counting the hybrids manufactured.

Thus, the recognition molecules 2 are combined with magnetic particles (Immunicon Streptavidine; Huntingdon Valley, USA, ref. F3106; diameter 145 nm; concentration $10^9$ p/ml) while the detection molecules 4 are combined with fluorescent nanoparticles (Molecular Probes Neutravidine; diameter 100 nm; concentration $10^9$ p/ml).

In a first stage, the target molecules 3 are hybridized with the fluorescent detection molecules 4. The target molecules 3 (concentration: $10^6$ p/μl) are incubated at room temperature for 4 hours with the detection molecules 4 (concentration: 1 nM) in TE buffer containing 1 M NaCl and 0.05% Triton (final volume: 20 μl).

In a second stage, the target molecules 3 hybridized with the detection molecules 4 are incubated for 1 hour at room temperature with the recognition molecules 2 combined with the magnetic particles. The target molecules 3 are thus sandwiched between a magnetizable recognition molecule 2 and a fluorescent detection molecule 4.

In a third stage, the double hybrids are observed under a microscope with epifluorescence illumination or with dark field illumination. A device with a permanent magnet, placed under the plate of the microscope, makes it possible to apply a magnetic field of 300 Gauss. Under the action of this magnetic field, the magnetic particles assemble in the form of rods into which fluorescent particles may be incorporated. However, at this stage of the test, it cannot be concluded whether these conjugates incorporate a target molecule or otherwise.

In a fourth stage, this uncertainty is removed at an oriented dissociation stage. For this, the buffer for suspending the particles is replaced, under a magnetic confining field, by a low ionic strength TE buffer containing 0.05% Triton X100, and the particles are heated at 70° C. for 30 minutes.

Immediately afterwards, a magnetic washing is carried out. The suspension obtained is examined under a microscope, still under a magnetic field of 300 Gauss. The combination of the ionic strength and the temperature therefore made it possible to separate the target molecules 3 from the detection molecules 4. The level of dissociation depends on the exact nature of the functionalizations of the two types of nanoparticles and also on the length and the sequence of the DNA molecules, and on the composition of the buffer.

This mode of application of oriented dissociation between a fluorescent particle and a magnetic particle, or more precisely between a target molecule 3 and a detection molecule 4, can be carried out with other types of nonmagnetic or non-fluorescent particles, or with particles whose functionalization is different, or with particles of different sizes.

EXAMPLE 4

Oriented Dissociation of the Labeled Target Molecules in Relation to the Recognition Molecules The main characteristic of this example is to directly use labeled target molecules without having recourse to detection molecules for detecting the hybridization between the recognition molecules and the target molecules. The model consists of:
a recognition molecule, whose sequence is identical to that described in Example 1
a target molecule, whose sequence is identical to that described in Example 1, fragmented and labeled beforehand according to the protocol described in patent application PCT/FR99/01469.

Using this method, fragments of about 50 nucleotides, labeled at their 3' end with a fluorescent marker, are obtained. One of these fragments, called detection fragment can hybridize by complementarity with the recognition molecule according to a protocol similar to that which is described in Example 1.

Thus, the immobilization of the recognition molecules on the support is carried out as described in the first stage of Example 1. After immobilization of the recognition molecules, the hybridization of the recognition molecules with the labeled target molecules is carried out by incubating the support in TE containing 1 M NaCl.

The support 1 is then taken up, washed in this same buffer for 15 minutes at room temperature. This washing step is very important since it makes it possible to remove the fragments obtained by this method, which are the detection fragments which are not hybridized, and the fragments which do not possess the region complementary to the recognition molecule.

A first image is produced by fluorescence microscopy, as described in Example 2, which makes it possible to obtain the level of fluorescence due to the presence of true-positives, but also of false-positives.

The dissociation of the target molecules labeled with the recognition molecules is then carried out by incubating the support in a TE buffer containing 0.05% Triton X100, at 95° C. for 1 h.

A second image is then produced which makes it possible to detect the detection fragments which are only adsorbed at the surface and which were not properly hybridized with the recognition molecules, which constitute false-positives. As described in Example 1, by subtracting the detection spots present on the 1st image from those of the 2nd image, it is possible to distinguish between the presence of true-positives and false-positives.

Still with the aim of checking the results obtained in the preceding stages, the support to which the recognition molecules are attached is incubated a second time with the target molecules under conditions identical to the first recognition molecule—target molecule hybridization described above, and the support is washed in TE buffer containing 1 M NaCl, 0.05% Triton X100 for 15 minutes at room temperature.

A 3rd image makes it possible to verify the distinction made between the true-positives and the false-positives. Furthermore, this 3rd image makes it possible to verify that said recognition molecules are still present on the support since the same intensity of the detection signal is obtained as that for the 1st image. Consequently, the recognition molecules need not become dissociated from the support.

REFERENCES

1. Biochip support 5
2. Recognition molecule
3. Target molecule
4. Detection molecule
5. Biochip
6. Nonhybridized or noncomplexed target molecule
7. Target molecule hybridized or complexed elsewhere than on a recognition molecule 2
8. Nonhybridized or noncomplexed detection molecule
9. Detection molecule adsorbed or complexed elsewhere than on a target molecule 3
10. First image
11. Second image
12. Third image
13. Fourth image
14. Detection spot corresponding to a detection molecule 4, 8 or 9
15. Position of a detection spot which has disappeared, corresponding to a detection molecule 4
16. Detection spot corresponding to a detection molecule 9
17. Detection spot which has just appeared, corresponding to a detection molecule 9
18. Detection spot corresponding to a detection molecule 4

---

The invention claimed is:

1. A method of analyzing a support for at least one biological reaction, comprising:
   (a) bringing a support into contact with at least one first liquid sample comprising at least one group of identical biological recognition molecules so as to attach the recognition molecules to the support at the level of a recognition zone, such that the support is functionalized;
   b) bringing the functionalized support into contact with at least one second liquid sample comprising at least one labeled target biological molecule so as to attach the labeled target to the recognition molecules;
   (c) producing a first image of the support after the attachment of the labeled target showing detection spots;
   (d) separating the labeled target from the recognition molecules to which the labeled target is specifically attached;
   (e) producing a second image of the support after the separation in (d) showing detection spots; and
   (f) analyzing the first and second images to determine the specific attachments between the recognition molecules and labeled target by identifying true-positive and false-positive results by subtracting the detection spots present in the second image from the detection spots present in the first image.

2. The method as claimed in claim 1, wherein at least one washing step is carried out after the attachment of the recognition molecules to the support and/or after the attachment of the labeled target to the recognition molecules.

3. The method as claimed in claim 2, wherein the support comprises magnetic particles.

4. The method as claimed in claim 3, further comprising magnetizing the magnetic particles on the support during the step of separating the labeled target from the recognition molecules, during image production, or before any of the washing steps.

5. The method as claimed in claim 1, wherein the support is brought into contact with at least two different first liquid samples, thereby allowing for the attachment of at least two different groups of recognition molecules to the support in at least two distinct recognition zones.

6. The method as claimed in claim 1, further comprising:
   (g) bringing the support, after the separation in (d), into contact with the same at least one second liquid sample so as to reattach the labeled target to the recognition molecules from which it had been separated, or into contact with a different second liquid sample so as to attach the labeled target to other recognition molecules from the same recognition zone;
   (h) producing a third image of the support after the attachment of the labeled target in (g); and
   (i) analyzing the third image with respect to the analysis of the first and second images to confirm the specific attachments between the recognition molecules and labeled target by identifying true-positive and false-positive results.

7. The method as claimed in claim 6, wherein in the different second liquid sample, the at least one labeled target biological molecule has a different marker from that contained in the second liquid sample of step (b).

8. The method as claimed in claim 1, wherein the separating of d) is obtained by heating to a melting point.

9. The method as claimed in claim 1, wherein the labeled target or recognition molecules comprise nucleic acids, antibodies, or antigens.

10. The method as claimed in claim 1, wherein the labeled target is labeled for use with a method selected from the group consisting of optical microscopy, fluorescence microscopy, dark field microscopy, atomic force microscopy, electron microscopy, and thermal lens microscopy.

11. The method as claimed in claim 1, wherein the labeled target is labeled using an enzyme having a precipitating product which produces a detectable signal or using a chromophore.

12. The method as claimed in claim 11, wherein the detectable signal is detected by fluorescence or luminescence.

13. The method as claimed in claim 11, wherein the enzyme is selected from the group consisting of horseradish peroxidase, alkaline phosphatase, β-galactosidase, and glucose-6-phosphate dehydrogenase.

14. The method as claimed in claim 11, wherein the chromophore is a fluorescent compound or a luminescent compound.

15. A method of analyzing a support for at least one biological reaction, comprising:
   (a) mixing at least one first liquid sample comprising at least one group of identical biological recognition molecules and at least one second liquid sample comprising at least one labeled target biological molecule so as to attach the labeled target to the recognition molecules;
   (b) bringing a support into contact with the mixture of the first and second liquid samples so as to attach the recognition molecules to the support at the level of a recognition zone, such that the support is functionalized;
   (c) producing a first image of the support after the attachment of the labeled target showing detection spots;
   (d) separating the labeled target from the recognition molecules to which the labeled target is specifically attached;
   (e) producing a second image of the support after the separation in (d) showing detection spots; and
   (f) analyzing the first and second images to determine the specific attachments between the recognition molecules and labeled target by identifying true-positive and false-positive results by subtracting the detection spots present in the second image from the detection spots present in the first image.

16. The method as claimed in claim 15, further comprising:
   (g) bringing the support, after the separation in (d), into contact with the same at least one second liciuid sample so as to reattach the labeled target to the recognition molecules from which it had been separated, or into contact with a different second liquid sample so as to attach the labeled target to other recognition molecules from the same recognition zone;

(h) producing a third image of the support after the attachment of the labeled target in (g); and (i) analyzing the third image with respect to the analysis of the first and second images to confirm the specific attachments between the recognition molecules and the labeled target by identifying true-positive and false-positive results.

17. The method as claimed in claim 16, wherein in the different second liquid sample, the at least one labeled target biological molecule has a different marker from that contained in the second liquid sample of step (b).

18. A method of analyzing a support for at least one biological reaction, comprising:

(a) bringing a support into contact with at least one first liquid sample comprising at least one group of identical biological recognition molecules so as to attach the recognition molecules to the support at the level of a recognition zone, such that the support is functionalized;

(b) bringing the functionalized support into contact with at least one second liquid sample comprising at least one biological target molecule so as to attach the taget to the recognition molecules;

(c) bringing the functionalized support into contact with at least one third liquid sample comprising at least one labeled detection molecule so as to attach the labeled detection molecule to the target attached to the recognition molecules;

(d) producing a first image of the support after the attachment of the labeled detection molecule showing detection spots;

(e) separating the labeled detection molecule from the target to which the labeled detection molecule is specifically attached;

(f) producing a second image of the support after the separation in (e) showing detection spots; and (g) analyzing the first and second images to determine the specific attachments between the target and the labeled detection molecule by identifying true-positive and false-positive results by subtracting the detection spots present in the second image from the detection spots present in the first image.

19. The method as claimed in claim 18, wherein at least one washing step is carried out after the attachment of the recognition molecules to the support, after the attachment of the target to the recognition molecules, and/or after the attachment of the labeled detection molecule to the target.

20. The method as claimed in claim 19, wherein the support comprises magnetic particles.

21. The method as claimed in claim 20, further comprising magnetizing the magnetic particles on the support during step of separating the labeled detection molecule from the target, during image production, or before any of the washing steps.

22. The method as claimed in claim 18, wherein the support is brought into contact with at least two different first liquid samples, thereby allowing for the attachment of at least two different groups of recognition molecules to the support in at least two distinct recognition zones, wherein the different first liquid samples are combined prior to or after contact with the support.

23. The method as claimed claim 22, wherein the support is brought into contact with at least two different target molecules, thereby allowing for the quantification of said at least two different target molecules.

24. The method as claimed in claim 23, wherein the labeled detection molecule comprises a molecule combined with at least one marker which produces images that allow individual visualization.

25. The method as claimed in claim 24, wherein the at least one marker is a nanoparticle.

26. The method as claimed in claim 18, further comprising:

(h) bringing the support, after separation in (e), into contact with the same at least one third liquid sample so as to reattach the labeled detection molecule and target from which it had been separated, or into contact with a different third liquid sample so as to attach the labeled detection molecule to any other target attached to the recognition molecules from the same recognition zone;

(i) producing a third image of the support after the attachment of the labeled detection molecule in (h); and (j) analyzing the third image with respect to the analysis of the first and second images to confirm the specific attachments between the target and the labeled detection molecule by identifying true-positive and false-positive results.

27. The method as claimed in claim 26, wherein in the different third liquid sample, the labeled labeled detection molecule has a different marker from that contained in the third liquid sample of step (c).

28. The method as claimed in claim 18, wherein the separating of e) is obtained by heating to a melting point.

29. The method as claimed in claim 18, wherein the target, recognition molecules, or labeled detection molecule comprise nucleic acids, antibodies, or antigens.

30. The method as claimed in claim 18, wherein the labeled detection molecule is labeled for use with a method selected from the group consisting of optical microscopy, fluorescence microscopy, dark field microscopy, atomic force microscopy, electron microscopy, and thermal lens microscopy.

31. The method as claimed in claim 18, wherein the labeled detection molecule is labeled using an enzyme having a precipitating product which produces a detectable signal or using a chromophore.

32. The method as claimed in claim 31, wherein the detectable signal is detected by fluorescence or luminescence.

33. The method as claimed in claim 31, wherein the enzyme is selected from the group consisting of horseradish peroxidase, alkaline phosphatase, β-galactosidase, and glucose-6-phosphate dehydrogenase.

34. The method as claimed in claim 31, wherein the chromophore is a fluorescent compound or a luminescent compound.

35. A method of analyzing a support for at least one biological reaction, comprising:

(a) mixing at least one first liquid sample comprising at least one group of identical biological recognition molecules and at least one second liquid sample comprising at least one biological target molecule so as to attach the target to the recognition molecules;

(b) bringing a support into contact with the mixture of the first and second liquid samples so as to attach the recognition molecules to the support at the level of a recognition zone, such that the support is functionalized;

(c) bringing the functionalized support into contact with at least one third liquid sample comprising at least one labeled detection molecule so as to attach the labeled detection molecule to the target attached to the recognition molecules;

(d) producing a first image of the support after the attachment of the labeled detection molecule showing detection spots;

(e) separating the labeled detection molecule from the target to which the labeled detection molecule is specifically attached;

(f) producing a second image of the support after the separation in (e) showing detection spots; and (g) analyzing the first and second images to determine the specific attachments between the target and the labeled detection molecule by identifying true-positive and false-positive results by subtracting the detection spots present in the second image from the detection spots present in the first image.

36. The method as claimed in claim 35, further comprising:

(h) bringing the support, after separation in (e), into contact with the same at least one third liquid sample so as to reattach the labeled detection molecule and the target from which it had been separated, or into contact with a different third liquid sample so as to attach the labeled detection molecule to any other target attached to the recognition molecules from the same recognition zone;

(i) producing a third image of the support after the attachment of the labeled detection molecule in (h); and (j) analyzing the third image with respect to the analysis of the first and second images to confirm the specific attachments between the target and the labeled detection molecule by identifying true-positive and false-positive results.

37. The method as claimed in claim 36, wherein in the different third liquid sample, the labeled detection molecule has a different marker from that contained in the third liquid sample of step (c).

38. A method of analyzing a support for at least one biological reaction, comprising:

(a) mixing at least one first liquid sample comprising at least one group of identical biological recognition molecules and at least one second liquid sample comprising at least one biological target molecule so as to attach the target to the recognition molecules;

(b) adding at least one third liquid sample comprising at least one labeled detection molecule to the mixture of the first and second liquid samples so as to attach the labeled detection molecule to the target attached to the recognition molecules;

(c) bringing a support into contact with the mixture of the first, second, and third liquid samples so as to attach the recognition molecules to the support at the level of a recognition zone, such that the support is functionalized;

(d) producing a first image of the support after the attachment of the recognition molecules showing detection spots;

(e) separating the labeled detection molecule from the target to which the labeled detection molecule is specifically attached;

(f) producing a second image of the support after the separation in (e) showing detection spots; and (g) analyzing the first and second images to determine the specific attachments between the target and the labeled detection molecule by identifying true-positive and false-positive results by subtracting the detection spots present in the second image from the detection spots present in the first image.

39. The method as claimed in claim 38, further comprising:

(h) bringing the support, after separation in (e), into contact with the same at least one third liquid sample so as to reattach the labeled detection molecule and the target from which it had been separated, or into contact with a different third liquid sample so as to attach the labeled detection molecule to any other target attached to the recognition molecules from the same recognition zone;

(i) producing a third image of the support after the attachment of the labeled detection molecule in (h); and (j) analyzing the third image with respect to the analysis of the first and second images to confirm the specific attachments between the target and the labeled detection molecule by identifying true-positive and false-positive results.

40. The method as claimed in claim 39, wherein in the different third liquid sample, the labeled detection molecule has a different marker from that contained in the third liquid sample of step (c).

41. A method of analyzing a support for at least one biological reaction, comprising:

(a) mixing at least one second liquid sample comprising at least one target biological molecule and at least one third liquid sample comprising at least one labeled detection molecule so as to attach the target to the labeled detection molecule;

(b) adding at least one first liquid sample comprising at least one group of identical recognition molecules to the mixture of the second and third liquid samples so as to attach the recognition molecules to the target;

(c) bringing a support into contact with the mixture of the first, second, and third liquid samples so as to attach the recognition molecules to the support at the level of a recognition zone, such that the support is functionalized;

(d) producing a first image of the support after the attachment of the labeled detection molecule showing detection spots;

(e) separating the labeled detection molecule from the target to which the labeled detection molecule is specifically attached;

(f) producing a second image of the support after the separation in (e) showing detection spots; and (g) analyzing the first and second images to determine the specific attachments between the target and the labeled detection molecule by identifying true-positive and false-positive results by subtracting the detection spots present in the second image from the detection spots present in the first image.

42. The method as claimed in claim 41, further comprising:

(h) bringing the support, after separation in (e), into contact with the same at least one third liquid sample so as to reattach the labeled detection molecule and the target from which it had been separated, or into contact with a different third liquid sample so as to attach the labeled detection molecule to any other target attached to the recognition molecules from the same recognition zone;

(i) producing a third image of the support after the attachment of the labeled detection molecule in (h); and (j) analyzing the third image with respect to the analysis of the first and second images to confirm the specific attachments between the target and the labeled detection molecule by identifying true-positive and false-positive results.

43. The method as claimed in claim 42, wherein in the different third liquid sample, the labeled detection molecule has a different marker from that contained in the third liquid sample of step (a).

44. A method of analyzing a support for at least one biological reaction, comprising:

(a) bringing a support into contact with at least one first liquid sample comprising at least one group of identical biological recognition molecules so as to attach the recognition molecules to the support at the level of a recognition zone, such that the support is functionalized;

(b) mixing at least one second liquid sample comprising at least one target biological molecule and at least one third liquid sample comprising at least one labeled detection molecule so as to attach the target to the labeled detection molecule;

(c) bringing the mixture of the second and third liquid samples into contact with the support so as to attach the target to the recognition molecules;

(d) producing a first image of the support after the attachment of the labeled detection molecule showing detection spots;

(e) separating the labeled detection molecule from the target to which the labeled detection molecule is specifically attached;

(f) producing a second image of the support after the separation in (e) showing detection spots; and (g) analyzing the first and second images to determine the specific attachments between the target and the labeled detection molecule by identifying true-positive and false-positive results by subtracting the detection spots present in the second image from the detection spots present in the first image.

45. The method as claimed in claim 44, further comprising:

(h) bringing the support, after separation in (e), into contact with the same at least one third liquid sample so as to reattach the labeled detection molecule and the target from which it had been separated, or into contact with a different third liquid sample so as to attach the labeled detection molecule to any other target attached to the recognition molecules from the same recognition zone;

(i) producing a third image of the support after the attachment of the labeled detection molecule in (h); and (j) analyzing the third image with respect to the analysis of the first and second images to confirm the specific attachments between the target and the labeled detection molecule by identifying true-positive and false-positive results.

46. The method as claimed in claim 45, wherein in the different third liquid sample, the labeled detection molecule has a different marker from that contained in the third liquid sample of step (b).

* * * * *

SEQUENCE LISTING

```
<160> NUMBER OF SEQ ID NOS: 3

<210> SEQ ID NO 1
<211> LENGTH: 70
<212> TYPE: DNA
<213> ORGANISM: Artificial Sequence
<220> FEATURE:
<223> OTHER INFORMATION: recognition molecule

<400> SEQUENCE: 1
tcactattat cttgtattac tactgcccct tcacctttcc agaggagctt tgctggtcct     60
ttccaaagtg                                                            70

<210> SEQ ID NO 2
<211> LENGTH: 514
<212> TYPE: DNA
<213> ORGANISM: Artificial Sequence
<220> FEATURE:
<223> OTHER INFORMATION: target molecule

<400> SEQUENCE: 2
acagcagtac aaatggcagt attcatccac aattttaaaa gaaaggggg gattgggggg      60 tacagtgcag gggaaagaat agtagacata atagcaacag acatacaaac taaagaatta    120
caaaaacaaa ttacaaaaat tcaaaatttt cgggtttatt acagggacag cagaaatcca    180
ctttggaaag gaccagcaaa gctcctctgg aaaggtgaag gggcagtagt aatacaagat    240
aatagtgaca taaagtagt gccaagaaga aaagcaaaga tcattaggga ttatggaaaa     300
cagatggcag gtgatgattg tgtggcaagt agacaggat agattagaac atggaaaagt    360
ttagtaaaac accatatgta tgtttcaggg aaagctaggg gatggtttta tagacatcac   420
tatgaaagcc ctcatccaag aataagttca gaagtaaatc gaattcccgc ggccatggcg   480
gccgggagca tgcgacgtcg ggcccaattc gccc                              514

<210> SEQ ID NO 3
<211> LENGTH: 16
<212> TYPE: DNA
<213> ORGANISM: Artificial Sequence
```

-continued

```
<220> FEATURE:
<223> OTHER INFORMATION: detection molecule

<400> SEQUENCE: 3
ttctgaactt attctt                                                         16
```